United States Patent
Blizzard et al.

(10) Patent No.: US 9,133,147 B2
(45) Date of Patent: Sep. 15, 2015

(54) THROMBIN INHIBITORS

(71) Applicant: Merck Sharp & Dohme Corp., Rahway, NJ (US)

(72) Inventors: Timothy Allen Blizzard, Princeton, NJ (US); Tesfaye Biftu, Freehold, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/387,977

(22) PCT Filed: Mar. 22, 2013

(86) PCT No.: PCT/US2013/033399
§ 371 (c)(1),
(2) Date: Sep. 25, 2014

(87) PCT Pub. No.: WO2013/148478
PCT Pub. Date: Oct. 3, 2013

(65) Prior Publication Data
US 2015/0038498 A1    Feb. 5, 2015

Related U.S. Application Data

(60) Provisional application No. 61/616,647, filed on Mar. 28, 2012.

(51) Int. Cl.
| | |
|---|---|
| *C07D 295/18* | (2006.01) |
| *C07D 241/04* | (2006.01) |
| *C07D 265/30* | (2006.01) |
| *C07D 279/12* | (2006.01) |
| *C07D 211/60* | (2006.01) |
| *A61K 31/497* | (2006.01) |
| *A61K 9/00* | (2006.01) |
| *A61K 47/12* | (2006.01) |
| *A61K 9/20* | (2006.01) |

(52) U.S. Cl.
CPC ............ *C07D 295/18* (2013.01); *A61K 9/0019* (2013.01); *A61K 9/2054* (2013.01); *A61K 47/12* (2013.01); *C07D 211/60* (2013.01); *C07D 241/04* (2013.01); *C07D 265/30* (2013.01); *C07D 279/12* (2013.01)

(58) Field of Classification Search
CPC .. C07D 295/18; C07D 241/04; C07D 265/30; C07D 279/12; C07D 211/60; A61K 31/497
USPC ....................................... 544/58.4; 514/227.5
See application file for complete search history.

(56) References Cited

U.S. PATENT DOCUMENTS 5,977,114 A    11/1999    Oh et al.

FOREIGN PATENT DOCUMENTS

WO    W09715190    5/1997

OTHER PUBLICATIONS

Reister, D., et al., Thrombin inhibitors identified by computer-assisted multiparameter design, PNAS, 102 (24); (2005), pp. 8597-8602.
International Search Report for PCT/US2013/33399, dated Mar. 22, 2013; 2 pages.

*Primary Examiner* — Kahsay Habte
(74) *Attorney, Agent, or Firm* — Nicole M. Beeler; Catherine D. Fitch

(57)    ABSTRACT

Compounds of the invention are useful in inhibiting thrombin and associated thrombotic occlusions having the following structure:

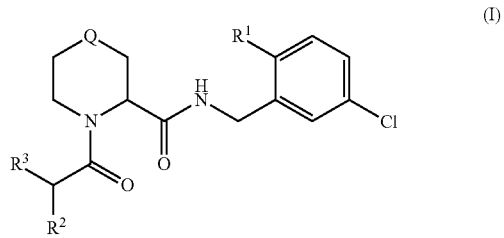

or a pharmaceutically acceptable salt thereof, wherein
Q is $CH_2$, $NR^4$, O, S, S(O) or $S(O_2)$, wherein $R^4$ is H, $C_{1-6}$ alkyl, aryl, or $C_{3-8}$ cycloalkyl;
$R^1$ is a heterocycle or $—(CR^5R^6)_{1-2}NH_2$, wherein $R^5$ and $R^6$, each time in which they occur, are independently H, $C_{1-6}$ alkyl, $—CH_2F$, $—CHF_2$, $CF_3$ or $—CH_2OH$;
$R^2$ is OH, $NH_2$ or $NHSO_2CH_3$;
$R^3$ is $C_{1-6}$ alkyl.

18 Claims, No Drawings

THROMBIN INHIBITORS

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., J. Amer. Chem. Soc., (1992) vol. 114, pp. 1854-63, describes peptidyl α-ketobenzoxazoles which are reversible inhibitors of the serine proteases human leukocyte elastase and porcine pancreatic elastase. European Publication 363 284 describes analogs of peptidase substrates in which the nitrogen atom of the scissile amide group of the substrate peptide has been replaced by hydrogen or a substituted carbonyl moiety. Australian Publication 86245677 also describes peptidase inhibitors having an activated electrophilic ketone moiety such as fluoromethylene ketone or α-keto carboxyl derivatives. R. J. Brown et al., J. Med. Chem., Vol. 37, pages 1259-1261 (1994) describes orally active, non-peptidic inhibitors of human leukocyte elastase which contain trifluoromethylketone and pyridinone moieties. H. Mack et al., J. Enzyme Inhibition, Vol. 9, pages 73-86 (1995) describes rigid amidino-phenylalanine thrombin inhibitors which contain a pyridinone moiety as a central core structure.

SUMMARY OF THE INVENTION

The invention includes compounds for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compounds may optionally include anticoagulants, antiplatelet agents, and thrombolytic agents. The compounds can be added to blood, blood products, or mammalian organs in order to effect the desired inhibitions.

The invention also includes a compound for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compounds may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

DETAILED DESCRIPTION OF THE INVENTION

Compounds of the invention are useful as thrombin inhibitors and have therapeutic value in for example, preventing coronary artery disease. The invention includes compounds of formula I:

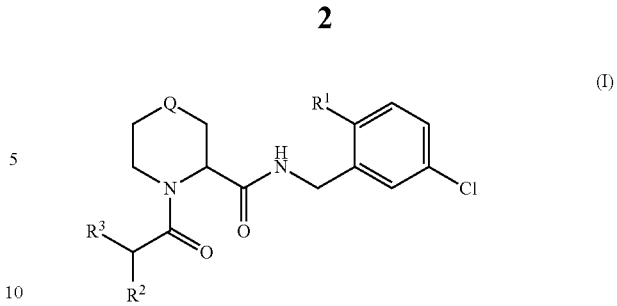

or a pharmaceutically acceptable salt thereof, wherein
Q is $CH_2$, $NR^4$, O, S, S(O) or $S(O_2)$, wherein $R^4$ is H, $C_{1-6}$ alkyl, aryl, or $C_{3-8}$ cycloalkyl;
$R^1$ is a heterocycle or $-(CR^5R^6)_{1-2}NH_2$, wherein $R^5$ and $R^6$, each time in which they occur, are independently H, $C_{1-6}$ alkyl, $-CH_2F$, $-CHF_2$, $CF_3$ or $-CH_2OH$;
$R^2$ is OH, $NH_2$ or $NHSO_2CH_3$;
$R^3$ is $C_{1-6}$ alkyl.

In one embodiment of the invention, the compounds, and pharmaceutically acceptable salts thereof, have the structure of formula Ia:

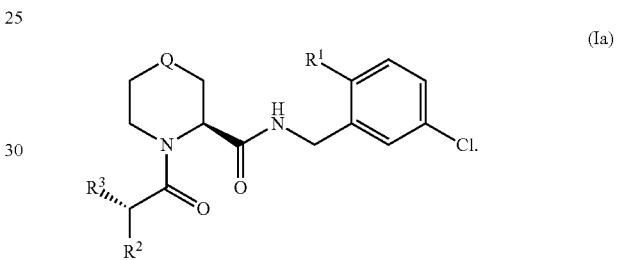

In another embodiment of the invention, $R^1$ is tetrazole or $-CH_2NH_2$. In a class of this embodiment, $R^1$ is $-CH_2NH_2$.
In another embodiment of the invention, $R^2$ is OH.
In another embodiment of the invention, $R^3$—$C(CH_3)_3$.
In another embodiment of the invention, $R^4$ is H or $CH_3$.
In another embodiment of the invention, $R^5$ is H.
In another embodiment of the invention, $R^6$ is H.
In another embodiment of the invention, the compounds, and pharmaceutically acceptable salts thereof, have the structure of formula Ib:

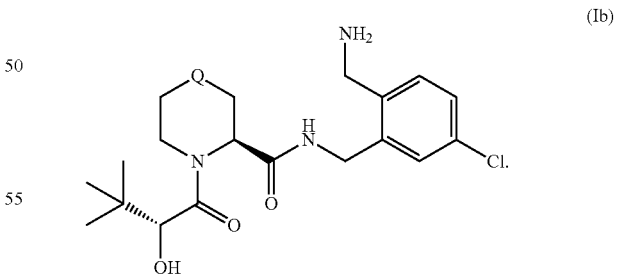

In another embodiment of the invention, the compound is
(2S)—N-[2-(aminomethyl)-5-chlorobenzyl]-1-[(2R)-2-hydroxy-3,3-dimethylbutanoyl]piperidine-2-carboxamide,
(2S)—N-[2-(aminomethyl)-5-chlorobenzyl]-1-[(2R)-2-hydroxy-3,3-dimethylbutanoyl]piperazine-2-carboxamide,
(2S)—N-[2-(aminomethyl)-5-chlorobenzyl]-1-[(2R)-2-hydroxy-3,3-dimethylbutanoyl]-4-methylpiperazine-2-carboxamide, (3 S)—N-[2-(aminomethyl)-5-chlorobenzyl]-4-[(2R)-2-hydroxy-3,3-dimethylbutanoyl]morpholine-3-carboxamide, (3R)—N-[2-(aminomethyl)-5-chlorobenzyl]-4-[(2R)-2-hydroxy-3,3-dimethylbutanoyl]thiomorpholine-3-carboxamide, (3R)—N-[2-(aminomethyl)-5-chlorobenzyl]-4-[(2R)-2-hydroxy-3,3-dimethylbutanoyl]thiomorpholine-3-carboxamide 1-oxide, or (3R)—N-[2-(aminomethyl)-5-chlorobenzyl]-4-[(2R)-2-hydroxy-3,3-dimethylbutanoyl]thiomorpholine-3-carboxamide 1,1-dioxide, or a pharmaceutically acceptable salt thereof In a class of this embodiment, the salt is (2S)—N-[2-(aminomethyl)-5-chlorobenzyl]-1-[(2R)-2-hydroxy-3,3-dimethylbutanoyl]piperidine-2-carboxamide trifluoroacetate, (2S)—N-[2-(aminomethyl)-5-chlorobenzyl]-1-[(2R)-2-hydroxy-3,3-dimethylbutanoyl]piperazine-2-carboxamide bis trifluoroacetate, (2S)—N-[2-(aminomethyl)-5-chlorobenzyl]-1-[(2R)-2-hydroxy-3,3-dimethylbutanoyl]-4-methylpiperazine-2-carboxamide trifluoroacetate, (3S)—N-[2-(aminomethyl)-5-chlorobenzyl]-4-[(2R)-2-hydroxy-3,3-dimethylbutanoyl]morpholine-3-carboxamide trifluoroacetate, (3R)—N-[2-(aminomethyl)-5-chlorobenzyl]-4-[(2R)-2-hydroxy-3,3-dimethylbutanoyl]thiomorpholine-3-carboxamide trifluoroacetate, (3R)—N-[2-(aminomethyl)-5-chlorobenzyl]-4-[(2R)-2-hydroxy-3,3-dimethylbutanoyl]thiomorpholine-3-carboxamide 1-oxide trifluoroacetate, or (3R)—N-[2-(aminomethyl)-5-chlorobenzyl]-4-[(2R)-2-hydroxy-3,3-dimethylbutanoyl]thiomorpholine-3-carboxamide 1,1-dioxide trifluoroacetate.

The present invention encompasses all stereoisomeric forms of the compounds of Formula I. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Reference to the compounds of this invention as those of a specific formula or embodiment, e.g., Formula I or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of structural Formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically acceptable salts.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO⁻ depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, prodrug forms thereof, and salts of pro-drug forms thereof, where such forms are possible unless specified otherwise.

When any variable occurs more than one time in any constituent or in formula I, its definition on each occurrence is independent of its definition at every other occurrence. Also, combinations of substituents and/or variables are permissible only if such combinations result in stable compounds.

Some abbreviations that may appear in this application are as follows:

ABBREVIATIONS

BOC tert-butyloxycarbonyl
(BOC)$_2$O di-t-butyl dicarbonate
CBZ benzyloxycarbonyl
CBZ-Cl benzyl chloroformate
DCC N,N'-dicyclohexylcarbodiimide
DMAP dimethylaminopyridine
DMF dimethylformamide
EDC 1-ethyl-3-(3-dimethylaminopropyl)carbodiimide
EtOAc ethyl acetate
FMOC 9-fluorenylmethoxycarbonyl
HOBT 1-hydroxybenzotriazole
MTBE methyl tert-butyl ether
pna p-nitroanilide
OAc acetoxy group
PEG polyethylene glycol
PyBOP (Benzotriazol-1-yloxy)tripyrrolidinophosphonium hexafluorophosphate
THF tetrahydrofuran
TRIS tris(hydroxymethyl)aminomethane
Z-GPR-afc Z-Gly-Pro-Arg-7-amino-4-trifluoromethylcoumarin Except where noted, the term "alkyl" refers to both branched- and straight-chain saturated aliphatic hydrocarbon groups having the specified number of carbon atoms (Me is methyl, Et is ethyl, Pr is propyl, Bu is butyl), unsubstituted or substituted with $C_{1-4}$ alkyl or halogen.

Except where noted, the term "$C_{3-8}$ cycloalkyl" refers to cyclopropyl, cyclobutyl, cyclopentyl, cyclohexyl, cycloheptyl, and cyclooctyl, and the like, unsubstituted or substituted with $C_{1-4}$ alkyl or halogen.

Except where noted, the term "aryl" refers to a stable 6- to 10-membered mono- or bicyclic ring system such as phenyl, or naphthyl. The aryl ring can be unsubstituted or substituted with one or more of $C_{1-4}$ alkyl, hydroxyl, alkoxy, halogen, or amino.

Except where noted, the term "heterocycle" or "heterocyclic ring" refers to a stable 5- to 7-membered mono- or bicyclic or stable 7- to 10-membered bicyclic heterocyclic ring system unsubstituted or substituted with $C_{1-4}$ alkyl or halogen, any ring of which may be saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyridyl N-oxide, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, tetrazole, thienyl, benzothienyl, thiamorpholinyl, thiamorpholinyl sulfoxide, thiamorpholinyl sulfone, and oxadiazolyl. Morpholino is the same as morpholinyl.

In this specification methyl substituents may be represented by

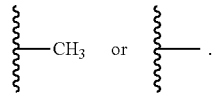

For example, the structures

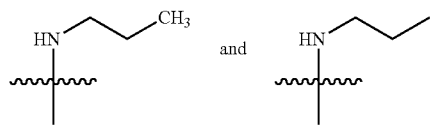

have equivalent meanings.

Thrombin Inhibitors—Therapeutic Uses—Method of Using

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention are useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention are useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention are useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the thrombin inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The thrombin inhibitors can also be co-administered with suitable anticoagulants, including, but not limited to, other thrombin inhibitors, thrombin receptor antagonists, factor VIIa inhibitors, factor IXa inhibitors, factor Xa inhibitors, factor XIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Also, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter.

Alternatively or additionally, one or more additional pharmacologically active agents may be administered in combination with a compound of Formula I. The additional active agent (or agents) is intended to mean a pharmaceutically active agent (or agents) that is active in the body, including pro-drugs that convert to pharmaceutically active form after administration, which is different from the compound of Formula I, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs (e.g., losartan i.e., COZAAR®, valsartan, candesartan, olmesartan, telmesartan, eprosartan, irbesartan and any of these drugs used in combination with hydrochlorothiazide such as HYZAAR®); diuretics, e.g. hydrochlorothiazide (HCTZ); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892; A 65317; CP 80794; ES 1005; ES 8891; SQ 34017; aliskiren (2(S),4 (S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTIVE®) and/or with an HMG-CoA reductase inhibitor; niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide; and including the free-acid, free-base, and pharmaceutically acceptable salt forms of the above active agents where chemically possible.

Typical doses of thrombin inhibitors of the invention in combination with other suitable anti-platelet agents, anticoagulation agents, or thrombolytic agents may be the same as those doses of thrombin inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

Compounds claimed in this invention can be prepared according to the following general procedure.

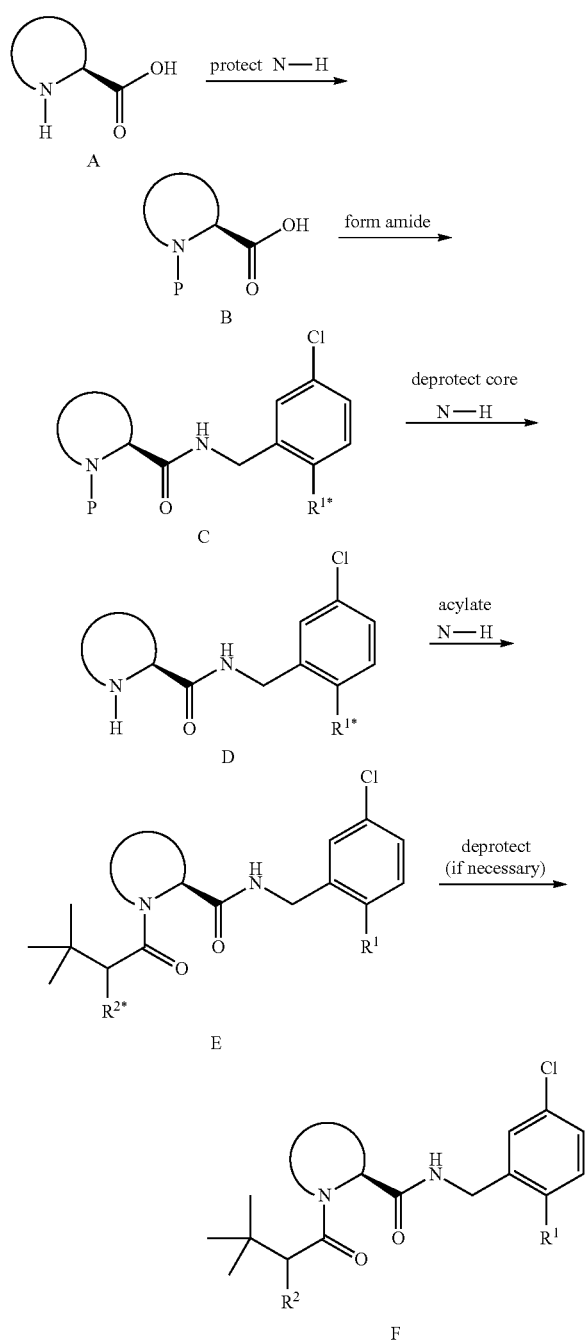

P = amine protecting group; R$^{2*}$ = protected (if necessary) version of R$^2$; R$^{1*}$ = protected (if necessary) version of R$^1$ The compounds of the instant invention can be prepared by methods known to those skilled in the art. The synthesis generally begins with the core amino-acid A. The N—H group is protected using a standard amine protecting group such as BOC, FMOC, CBZ, and the like by reacting the amine with the appropriate protecting reagent such as (BOC)$_2$O, FMOC-Cl, CBZ-Cl, and the like at a temperature of 0-35° C. in an appropriate solvent such as THF, dioxane, ether, dichloromethane, and the like, with or without added base such as NaHCO$_3$, Et$_3$N, and the like for a period of 1-24 hours. In cases where the core contains an additional amino group, the second amine is protected with an orthogonal protecting group such as BOC, FMOC, CBZ, and the like using standard techniques known to those skilled in the art. Upon completion, the reaction mixture is diluted with water, acidified by addition of a strong acid such as hydrochloric acid, sulfuric acid, and the like, and extracted with an organic solvent such as ethyl acetate, ether, and the like. The product is isolated by evaporation of the solvent and may be purified by chromatography or used "as is" in the next step.

The second step of the synthesis involves coupling the core acid with an amine side chain to form an amide bond. This can be accomplished using standard amide bond-forming techniques well-known to those skilled in the art. The core acid and the side chain amine are dissolved or suspended in a suitable solvent such as DMF, THF, dichloromethane, and the like then a coupling agent such as EDC, DCC, PyBOP and the like is added and the reaction is allowed to proceed, with or without an additive such as HOBT, DMAP, and the like at a temperature of 0-35° C. for 1-24 hours. Upon completion, the reaction mixture is diluted with water, washed with a basic aqueous solution such as aqueous sodium bicarbonate, aqueous potassium carbonate, and the like and extracted with an organic solvent such as ethyl acetate, ether, and the like. The product is isolated by evaporation of the solvent and may be purified by chromatography or used "as is" in the next step.

The third step involves removal of the amine protecting group installed in step one using standard methods well-known to those skilled in the art. The fluorenylmethoxycarbonyl (FMOC) group, for example, is removed by dissolving the product of step two in an appropriate solvent such as dichloromethane, ether, and the like and adding an organic amine base such as piperidine, morpholine, and the like. The reaction mixture is stirred at a temperature of 0-35° C. for 1-24 hours then concentrated under vacuum. The residue is purified by silica gel chromatography or HPLC to afford the desired intermediate.

The fourth step involves installation of the "left-hand" side chain by forming an amide bond between the amine nitrogen of the amino-acid core and the acid of the side chain. This can be accomplished using standard amide bond-forming techniques well-known to those skilled in the art. The core amine and the side chain acid are dissolved or suspended in a suitable solvent such as DMF, THF, dichloromethane, and the like then a coupling agent such as EDC, DCC, PyBOP and the like is added and the reaction is allowed to proceed, with or without an additive such as HOBT, DMAP, and the like at a temperature of 0-35° C. for 1-24 hours. Upon completion, the reaction mixture is diluted with water, washed with a basic aqueous solution such as aqueous sodium bicarbonate, aqueous potassium carbonate, and the like and extracted with an organic solvent such as ethyl acetate, ether, and the like. The product is isolated by evaporation of the solvent and the crude product is purified by silica gel chromatography or HPLC.

The final step involves removal of any protecting groups present in the two side chains. In the case where R$^2$ and/or R$^1$ is an amino group, the amine nitrogen(s) will have been protected as a using a standard amine protecting group such as BOC, FMOC, CBZ, and the like. Such protecting groups can be removed using standard techniques well-known to those skilled in the art. When R$^1$ is a tetrazole, no protecting group is needed for that side chain and such compounds can be readily prepared using the procedures outlined above without a final protecting group removal. In instances where R$^2$ is a hydroxyl group, the hydroxyl will have been protected with a protecting group such as acetate, t-butyldimethylsilyl, and the like. Such protecting groups can be removed using standard techniques well-known to those skilled in the art. Once deprotection is complete, the final products can be purified by silica gel chromatography or HPLC. When R² is a sulfonamide, no protecting group is needed for that side chain and such compounds can be readily prepared using the procedures outlined above without a final protecting group removal.

Unless otherwise stated, all NMR determinations were made using 400 MHz field strength. Ki data was obtained according to the procedure described in Lewis, et al. Thromb. Res. 1993, 70, 173 (assays of human-thrombin and human trypsin), and Lewis, et al. Thromb. Haemostasis 1995, 74, 1107-1112.

EXAMPLE 1

(2S)—N-[2-(aminomethyl)-5-chlorobenzyl]-1-[(2R)-2-hydroxy-3,3-dimethylbutanoyl]piperidine-2-carboxamide trifluoroacetate salt

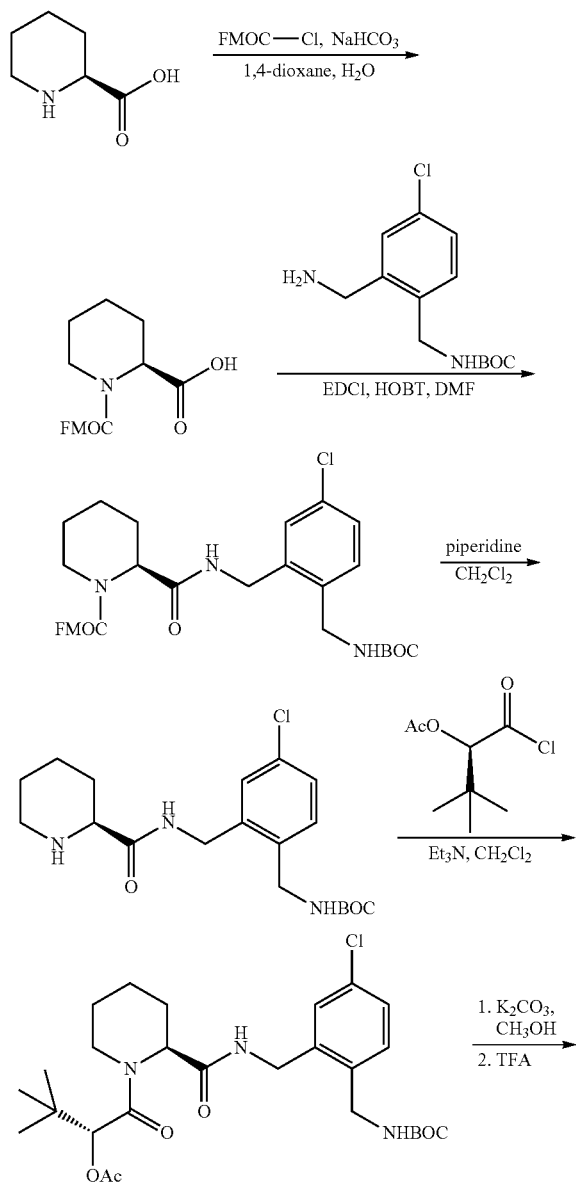

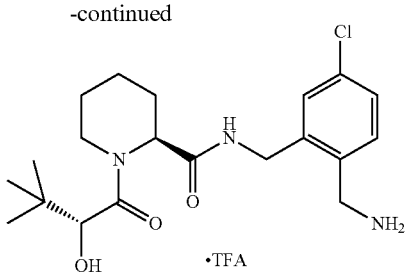

STEP 1: (S)-1-[{(9H-Fluoren-9-yl)methoxy}carbonyl]piperidine-2-carboxylic acid

To a stirred mixture of (S)-piperidine-2-carboxylic acid (1.0 g, 7.75 mmol) and Na₂CO₃ (1.65 g, 15.50 mmol) in water (10 mL) was added a solution of FMOC-Cl (3.0 g, 11.63 mmol) in 1,4-dioxane (10 mL) dropwise at 0° C. and the reaction mixture was stirred at room temperature for 16 h. The reaction mixture was diluted with water (50 mL) and washed with MTBE (25 mL). The aqueous layer was acidified with 1M aqueous HCl (10 mL) to pH 2 and extracted with EtOAc (3×50 mL). The combined organic extracts were washed with brine solution (50 mL), dried over anhydrous Na₂SO₄, filtered and concentrated to afford the title compound (1.41 g) as an off-white solid. The crude product was used in the next step without purification.

STEP 2: (S)-{9H-Fluoren-9-yl)methyl-2-[2-{(tert-butoxycarbonylamino)methyl}-5-chloro benzylcarbamoyl]piperidine-1-carboxylate A mixture of crude (S)-1-[{(9H-Fluoren-9-yl)methoxy}carbonyl]piperidine-2-carboxylic acid (0.75 g, 2.21 mmol), tert-butyl[2-(aminomethyl)-4-chlorobenzyl]carbamate (0.52 g, 1.93 mmol), HOBT (0.26 g, 1.93 mmol), and EDC.HCl (0.48 g, 2.51 mmol) in DMF (5 mL) was stirred under nitrogen at room temperature for 16 h. The reaction mixture was quenched with water (20 mL) and diluted with EtOAc (50 mL). The organic layer was washed sequentially with saturated aqueous NaHCO₃ solution (50 mL) and brine solution (50 mL), dried over anhydrous Na₂SO₄, filtered, and concentrated under reduced pressure. The residue was purified by reverse phase combiflash column chromatography (C18; eluent: 10-100% acetonitrile:water) to afford the title compound (0.89 g) as a white solid.

STEP 3: (S)-tert-Butyl-4-chloro-2-{(piperidine-2 carboxamido)methyl}-benzylcarbamate Piperidine (1.0 mL, 10.0 mmol) was added dropwise to a stirred solution of (S)-{9H-Fluoren-9-yl)methyl-2-[2-{(tert-butoxycarbonylamino)methyl}-5-chlorobenzylcarbamoyl]piperidine-1-carboxylate (0.89 g, 1.47 mmol) in CH₂Cl₂ (5 mL). The reaction mixture was stirred at room temperature for 1 h. Solvent was removed under reduced pressure and the crude product was purified by reverse phase combiflash column chromatography (C18; eluent: 10-100% acetonitrile:water) to afford the title compound (0.45 g) as a white solid.

STEP 4: (R)-1-{(S)-2-[2-{(tert-Butoxycarbonylamino)methyl}-5-chlorobenzylcarbamoyl]piperidin-1-yl}-3,3-dimethyl-1-oxobutan-2-yl acetate To a cooled (−10° C.) solution of (2R)-1-chloro-3,3-dimethyl-1-oxobutan-2-yl acetate (0.15 g, 0.82 mmol) in THF (5 mL) was added triethylamine (0.54 mL, 3.90 mmol) and a solution of (S)-tert-Butyl-4-chloro-2-{(piperidine-2-carboxamido)methyl}benzylcarbamate (0.3 g, 0.78 mmol) in THF (2 mL) at −10° C. The reaction mixture was stirred at room temperature for 1 h then quenched with water (50 mL) and extracted with EtOAc (3×25 mL). The combined organic extracts were washed with brine solution (50 mL), dried over anhydrous Na₂SO₄, filtered and concentrated. The residue was purified by reverse phase combiflash column chromatography (C18, eluent: 0-10% acetonitrile water) to afford the title compound (0.27 g) as a white solid.

STEP 5: (2S)—N-[2-(aminomethyl)-5-chlorobenzyl]-1-[(2R)-2-hydroxy-3,3-dimethylbutanoyl]piperidine-2-carboxamide trifluoroacetate salt Solid K₂CO₃ (7.5 mg, 0.052 mmol) was added to a solution of (R)-1-{(S)-2-[2-{(tert-butoxycarbonylamino)methyl}-5-chlorobenzylcarbamoyl]-piperidin-1-yl}-3,3-dimethyl-1-oxobutan-2-yl acetate (0.14 g, 0.26 mmol) in MeOH (5 mL) and the resulting mixture was stirred at room temperature for 30 min. The reaction mixture was diluted with EtOAc (50 mL) and washed sequentially with 0.1 N aqueous HCl (20 mL), water (2×20 mL), and brine solution (20 mL). The organic layer was dried over anhydrous Na₂SO₄, filtered and concentrated under reduced pressure. The residue was purified by reverse phase combiflash column chromatography (C18; eluent: 10-100% acetonitrile/water) to provide the intermediate BOC protected amino alcohol (0.12 g, crude) as an off-white solid. The crude intermediate was dissolved in CH₂Cl₂ (2 mL) then trifluoroacetic acid (0.5 mL, 27.20 mmol) was added. The reaction mixture was stirred at room temperature for 2 h then volatile byproducts were removed under reduced pressure residue. The residue was purified by reverse phase combiflash column chromatography (C18; eluent: 10-100% acetonitrile:water) to afford the title compound as a white solid. $^1$H NMR (MeOD, 400 MHz) (δ) ppm: 7.36-7.46 (m, 3H), 4.99-5.08 (m, 1H), 4.01-4.51 (m, 6H), 3.36-3.37 (m, 1H), 2.15-2.21 (m, 1H), 1.64-1.68 (m, 3H), 1.39-1.54 (m, 2H), 0.98 (s, 9H).

Ki (nM): 7.3

EXAMPLE 2

(2S)—N-[2-(aminomethyl)-5-chlorobenzyl]-1-[(2R)-2-hydroxy-3,3-dimethylbutanoyl]piperazine-2-carboxamide bis trifluoroacetate salt

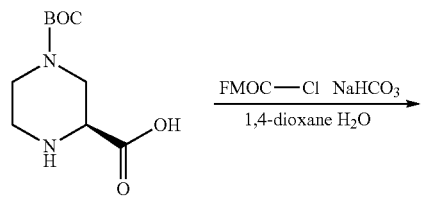

STEP 1: (S)-1-[((9H-Fluoren-9-yl)methoxy)carbonyl)-4-(tert-butoxycarbonyl)piperazine-2-carboxylic acid To a stirred mixture of (S)-4-(tert-butoxycarbonyl)piperazine-2-carboxylic acid (1.0 g, 4.34 mmol) and Na₂CO₃ (0.90 g, 10.80 mmol) in water (10 mL) was added solution of FMOC-Cl (1.23 g, 4.77 mmol) in 1,4-dioxane (10 mL) dropwise at 0° C. The reaction mixture was stirred at room temperature for 16 h then diluted with water (50 mL) and washed with MTBE (25 mL). The aqueous layer was acidified with 1N aqueous HCl (10 mL) to pH 2 and extracted with EtOAc (3×50 mL). The combined organic extracts were washed with brine solution (50 mL), dried over anhydrous Na₂SO₄, fil-

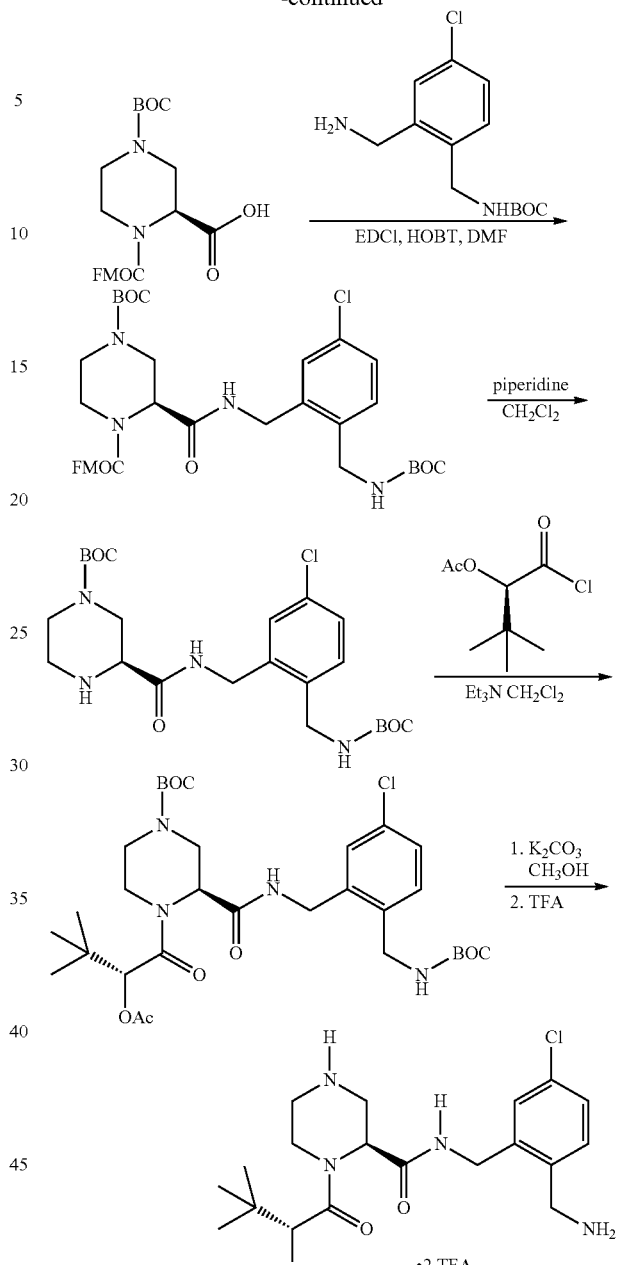

tered and concentrated to afford the title compound (0.87 g) as an off-white solid. The crude product was used in the next step without purification.

STEP 2: (S)-1-[((9H-Fluoren-9-yl)methyl-4-tert-butyl-2-[2-{(tert-butoxycarbonylamino)methyl}-5-chlorobenzylcarbamoyl]piperazine-1,4-dicarboxylate A mixture of (S)-1-[((9H-Fluoren-9-yl)methoxy)carbonyl)-4-(tert-butoxycarbonyl)piperazine-2-carboxylic acid (0.27 g, 1.0 mmol), tert-butyl[2-(aminomethyl)-4-chlorobenzyl]carbamate (0.5 g, 1.10 mmol), HOBT (0.135 g, 1 mmol), and EDC.HCl (0.25 g, 1.30 mmol) in anhydrous DMF (3 mL) was stirred under nitrogen at room temperature for 16 h. The reaction mixture was quenched with water (10 mL), diluted with EtOAc (25 mL) and washed sequentially with saturated aqueous NaHCO3 solution (25 mL) and brine solution (25 mL). The organic layer was separated, dried over anhydrous Na2SO4, filtered and concentrated. The residue was purified by reverse phase combiflash column chromatography (C18; eluent: 10-100% acetonitrile:water) to afford the title compound (0.61 g) as white solid.

STEP 3: (S)-tert-Butyl 3-[2-{(tert-butoxycarbonylamino)methyl}-5-chlorobenzylcarbamoyl]piperazine-1carboxylate Piperidine (0.5 mL, 5.06 mmol) was added to a stirred solution of (S)-1-[((9H-Fluoren-9-yl)methyl-4-tert-butyl-2-[2-{(tert-butoxycarbonylamino)methyl}-5-chlorobenzylcarbamoyl]-piperazine-1,4-dicarboxylate (0.60 g, 0.85 mmol) in CH2Cl2 (4 mL) and the reaction mixture was stirred at room temperature for 2 h. The solvent was removed under reduced pressure, and the residue was purified by reverse phase combiflash column chromatography (C18; eluent: 10-100% acetonitrile:water) to obtain the title compound (0.30 g) as a white solid.

STEP 4: (S)-tert-Butyl-4-{(R)-2-acetoxy-3,3-dimethylbutanoyl}-3-[2-{(tert-butoxycarbonyl amino)methyl}-5-chlorobenzylcarbamoyl]piperazine-1-carboxylate A solution of (R)-2-hydroxy-3,3-dimethylbutanoic acid (86.2 mg, 0.65 mmol) in acetyl chloride (0.15 mL, 2.11 mmol) was heated to 60° C. for 15 min. Excess acetyl chloride was removed under reduced pressure and the residue was dried under high vacuum. The residue was dissolved in thionyl chloride (0.15 mL, 2.06 mmol) and the mixture was heated at refluxed for 2 h. Volatile impurities were dissolved in THF (5 mL) and triethylamine (0.45 mL, 3.26 mmol) was added. A solution of (S)-tert-Butyl 3-[2-{(tert-butoxycarbonylamino)methyl}-5-chlorobenzylcarbamoyl]piperazine-1carboxylate (0.30 g, 0.62 mmol) in THF (2 mL) at −5° C. was then added and the reaction mixture was allowed to warm to room temperature and stirred at room temperature for 1 h. The reaction mixture was quenched with water (50 mL) and extracted with EtOAc (3×25 mL). The combined organic layers were washed with brine solution (50 mL) then dried over anhydrous Na2SO4, filtered and concentrated under reduced pressure. The residue was purified by reverse phase combiflash column chromatography (C18; eluent: 10-100% acetonitrile:water) to afford the title compound (0.2 g) as a white solid.

STEP 5: (2S)—N-[2-(aminomethyl)-5-chlorobenzyl]-1-[(2R)-2-hydroxy-3,3-dimethylbutanoyl]piperazine-2-carboxamide bis trifluoroacetate salt Solid K2CO3 (8.2 mg, 0.06 mmol) was added to a solution of (S)-tert-Butyl-4-{(R)-2-acetoxy-3,3-dimethylbutanoyl}-3-[2-{(tert-butoxycarbonyl amino)-methyl}-5-chlorobenzyl-carbamoyl]-piperazine-1-carboxylate (0.19 g, 0.30 mmol) in MeOH (5 mL) and reaction mixture was stirred at room temperature for 30 min. The reaction removed under reduced pressure and residue was dried under high vacuum. The residue was mixture was diluted with EtOAc (50 mL) and washed with 0.1 N aqueous HCl (20 mL), water (2×20 mL), and brine (20 mL). The organic layer was separated, dried over anhydrous Na2SO4, filtered and concentrated under reduced pressure. The residue was purified by reverse phase combiflash column chromatography (C18; eluent: 10-100% acetonitrile/water) to afford the BOC protected intermediate (0.13 g) as an off-white solid. This intermediate was dissolved in CH2Cl2 (3 mL) then trifluoroacetic acid (0.8 mL, 48 mmol) was added and the reaction mixture was stirred at room temperature for 2 h. The volatile byproducts were removed at reduced pressure and the residue was purified by reverse phase combiflash column chromatography (C18; eluent: 10-100% acetonitrile:water) to obtain the title compound as a white solid. $^1$H NMR (CD3CN, 300 MHz) (δ) ppm: 8.88-8.01 (m, 5H), 7.44-7.34 (m, 3H), 5.72-5.21 (m, 1H), 4.73-4.12 (m, 6H), 3.88-3.83 (m, 1H), 3.40-2.70 (m, 5H), 0.99 (brs, 9H).

Ki (nM): 63

EXAMPLE 3

(2S)—N-[2-(aminomethyl)-5-chlorobenzyl]-1-[(2R)-2-hydroxy-3,3-dimethylbutanoyl]-4-methylpiperazine-2-carboxamide trifluoroacetate salt

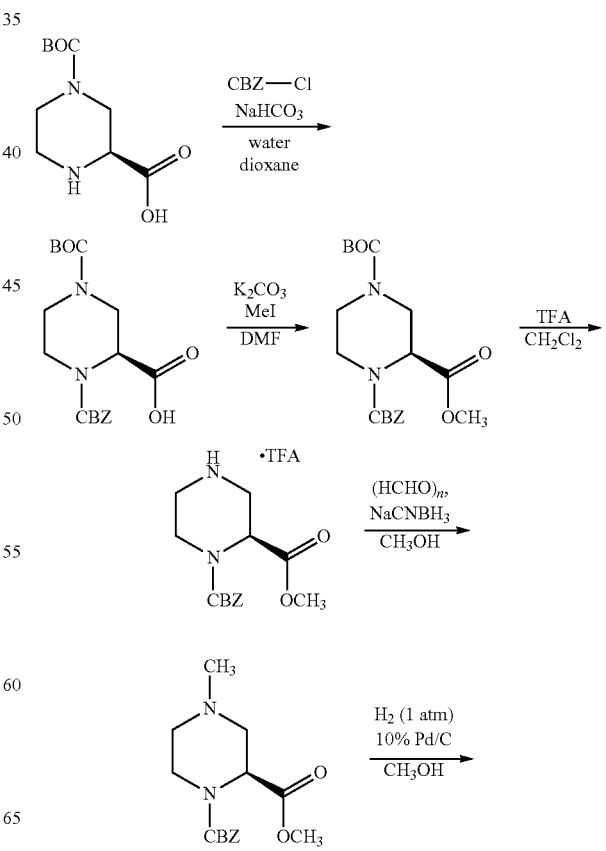

-continued

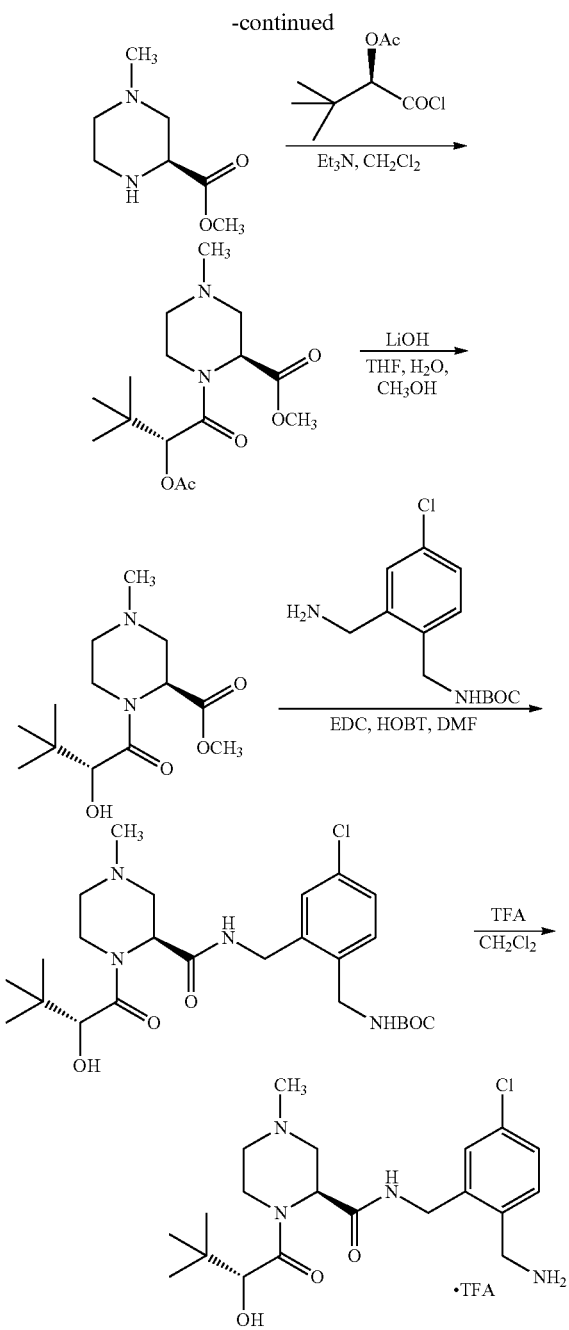

STEP 1: (S)-1-{(Benzyloxy)carbonyl}-4-(tert-butoxycarbonyl)piperazine-2-carboxylic acid To a stirred suspension of (S)-4-(tert-butoxycarbonyl) piperazine-2-carboxylic acid (1.0 g, 4.34 mmol) in water (5 mL) was added solid NaHCO₃ (0.73 g, 8.68 mmol) at room temperature. The reaction mixture was stirred at room temperature to get clear solution. Solution of CBZ-Cl (1.22 mL, 8.68 mmol) in 1,4-dioxane (10 mL) was added dropwise and the reaction mixture was stirred at room temperature for 16 h. The reaction mixture was diluted with water (20 mL) and extracted with EtOAc (2×20 mL). The aqueous layer was acidified with 0.5M aqueous HCl to pH 5 and extracted with EtOAc (2×50 mL). The combined organic layers were dried over anhydrous $Na_2SO_4$, filtered, and concentrated under reduced pressure to afford the title compound (1.30 g) as white solid.

STEP 2: (S)-1-Benzyl-2-methyl-4-methylpiperazine-1,2-dicarboxylate

To a stirred solution of (S)-1-{(benzyloxy)carbonyl}-4-(tert-butoxycarbonyl)piperazine-2-carboxylic acid (1.3 g, 3.57 mmol) in DMF (10 mL) was added $K_2CO_3$ (1.48 g, 10.71 mmol) and the reaction mixture was stirred at room temperature for 5 min. Methyl iodide (0.66 mL, 10.71 mmol) was added dropwise and the reaction mixture was stirred at room temperature for 2 h. The reaction was quenched with water (20 mL) and extracted with EtOAc (2×50 mL). The combined organic layer was dried over anhydrous $Na_2SO_4$, filtered, and concentrated under reduced pressure to afford the title compound (1.00 g) as a light yellow oil which was used in the next step without purification.

STEP 3: (S)-1-Benzyl-2-methyl piperazine-1,2-dicarboxylate

Trifluoroacetic acid (2.5 mL) was added to a stirred solution of (S)-1-Benzyl-2-methyl-4-methyl-piperazine-1,2-dicarboxylate (1.00 g, 2.63 mmol) in $CH_2Cl_2$ (5 mL) at room temperature and the reaction mixture was stirred at room temperature under nitrogen for 30 min. Solvent was removed under reduced pressure and the residue was azeotroped with toluene (2×30 mL), washed with diethyl ether (2×20 mL) and dried under high vacuum to afford the title compound (1.0 g) as an off-white hygroscopic solid.

STEP 4: (S)-1-Benzyl-2-methyl-4-methylpiperazine-1,2-dicarboxylate

To a stirred solution of (S)-1-Benzyl-2-methyl piperazine-1,2-dicarboxylate (1.0 g, 3.78 mmol) in MeOH (25 mL) was added triethylamine (0.52 mL, 3.78 mmol) and reaction mixture was cooled to 0° C. Paraformaldehyde (0.92 g, 11.36 mmol) was added to the reaction mixture followed by addition of a catalytic amount of acetic acid. The reaction mixture was stirred at room temperature for 1 h. $NaCNBH_3$ (0.35 g, 5.68 mmol) was added in portion at 0° C. and the reaction mixture was stirred at room temperature for 2 h. The solvent was removed at reduced pressure and the residue was dissolved in $CH_2Cl_2$ (50 mL) and washed with $NH_4OH$ solution (27% aqueous solution; 50 mL). The organic layer was separated, washed with water (2×50 mL) dried over anhydrous $Na_2SO_4$, filtered, and concentrated under reduced pressure to afford the title compound (0.52 g) as a colorless oil.

STEP 5: (S)-Methyl-4-methylpiperazine-2-carboxylate

Pd/C (0.05 g, 10% by wt) was added to the stirred solution of (S)-1-Benzyl-2-methyl-4-methylpiperazine-1,2-dicarboxylate (0.52 g, 1.787 mmol) in MeOH (25 mL) and the reaction mixture was stirred under an atmosphere of hydrogen (1 atm.) for 3 h. The reaction mixture was filtered through a pad of Celite, washed with MeOH (2×20 mL) and concentrated under reduced pressure. The residue was purified by reverse phase column chromatography (C18; eluent: 10%-40% water/acetonitrile) to afford the title compound (0.20 g) as a pale yellow hygroscopic solid.

STEP 6: (S)-Methyl-1-{(R)-2-acetoxy-3,3-dimethylbutanoyl}-4-methylpiperazine-2-carboxylate To a stirred solution of (2R)-1-chloro-3,3-dimethyl-1-oxobutan-2-yl acetate (0.247 g, 1.41 mmol) in CH$_2$Cl$_2$ (10 mL) was added triethylamine (0.39 mL, 2.83 mmol) and a solution of (S)-methyl-4-methylpiperazine-2-carboxylate (0.150 g, 0.943 mmol) in CH$_2$Cl$_2$ (3 mL) dropwise. The reaction mixture was stirred at room temperature for 30 minutes. Water (10 mL) was then added to quench the reaction and the reaction mixture was extracted with CH$_2$Cl$_2$ (2×25 mL). The combined organic layers were separated, washed with water (2×50 mL) dried over Na$_2$SO$_4$ and concentrated under reduced pressure to afford the title compound (0.12 g) as a white solid.

STEP 7: (S)-1-{(R)-2-Hydroxy-3,3-dimethylbutanoyl}-4-methylpiperazine-2-carboxylic acid A solution of LiOH (0.016 g, 0.66 mmol) in water (2 mL) was added to a stirred solution of (S)-methyl-1-{(R)-2-acetoxy-3,3-dimethylbutanoyl}-4-methylpiperazine-2-carboxylate (0.07 g, 0.22 mmol) in a 1:1 THF:MeOH mixture (3 mL) and the reaction mixture was stirred at room temperature for 2 h. The solvent was removed under reduced pressure and the residue was dissolved in water (10 mL), acidified with 1M aqueous HCl to pH 2-3 and extracted with EtOAc (2×20 mL). The combined organic layers were dried over anhydrous Na$_2$SO$_4$, filtered, and concentrated under reduced pressure to afford the title compound (0.034 g) as a colorless oil.

STEP 8: tert-Butyl 4-chloro-2-[{(S)-1-{(R)-2-hydroxy-3,3-dimethylbutanoyl}-4-methylpiperazine-2-carboxamido}methyl]benzylcarbamate A mixture of (S)-1-{(R)-2-Hydroxy-3,3-dimethylbutanoyl}-4-methylpiperazine-2-carboxylic acid (0.04 g, 0.15 mmol), 4-chloro-1,2-phenylene)dimethanamine (0.042 g, 0.15 mmol), EDCI (0.36 g, 0.186 mmol), HOBt (0.025 g, 0.18 mmol) and triethylamine (0.06 mL, 0.46 mmol) in CH$_2$Cl$_2$ (5 mL) was stirred at room temperature for 16 h. The reaction mixture was quenched with water (10 mL) and diluted with CH$_2$Cl$_2$ (2×20 mL). The organic layer was separated, washed with water (1×20 mL), dried over anhydrous Na$_2$SO$_4$, filtered, and concentrated under reduced pressure. The residue was purified by reverse phase column chromatography (C18, eluent: 10%-40% water/acetonitrile) to afford the title compound (0.025 g) as a white solid.

STEP 9: (2S)—N-[2-(aminomethyl)-5-chlorobenzyl]-1-[(2R)-2-hydroxy-3,3-dimethylbutanoyl]-4-methylpiperazine-2-carboxamide trifluoroacetate salt Trifluoroacetic acid (1 mL, 50% solution in CH$_2$Cl$_2$) was added to a solution of tert-Butyl 4-chloro-2-[{(S)-1-{(R)-2-hydroxy-3,3-dimethylbutanoyl}-4-methylpiperazine-2-carboxamido}methyl]benzylcarbamate (0.022 g, 0.0043 mmol) in CH$_2$Cl$_2$ (1 mL) and the reaction mixture was stirred under nitrogen for 1 h. The solvent was removed at reduced pressure and the residue was azeotroped with toluene (5 mL). The solid was washed with ether (2×4 mL) and dried under high vacuum to afford the title compound as a white hygroscopic solid. $^1$H NMR (MeOD-d$_4$, 300 MHz) (δ) ppm: 7.36-7.55 (m, 3H), 5.21-5.38 (m, 1H), 4.37-4.53 (m, 3H), 4.26-4.28 (m, 3H), 3.95-3.68 (m, 2H), 3.16-3.22 (m, 1H), 2.55-2.73 (m, 5H), 0.97 (s, 9H).
Ki (nM): 34

EXAMPLE 4

(3S)—N-[2-(aminomethyl)-5-chlorobenzyl]-4-[(2R)-2-hydroxy-3,3-dimethylbutanoyl]morpholine-3-carboxamide trifluoroacetate salt

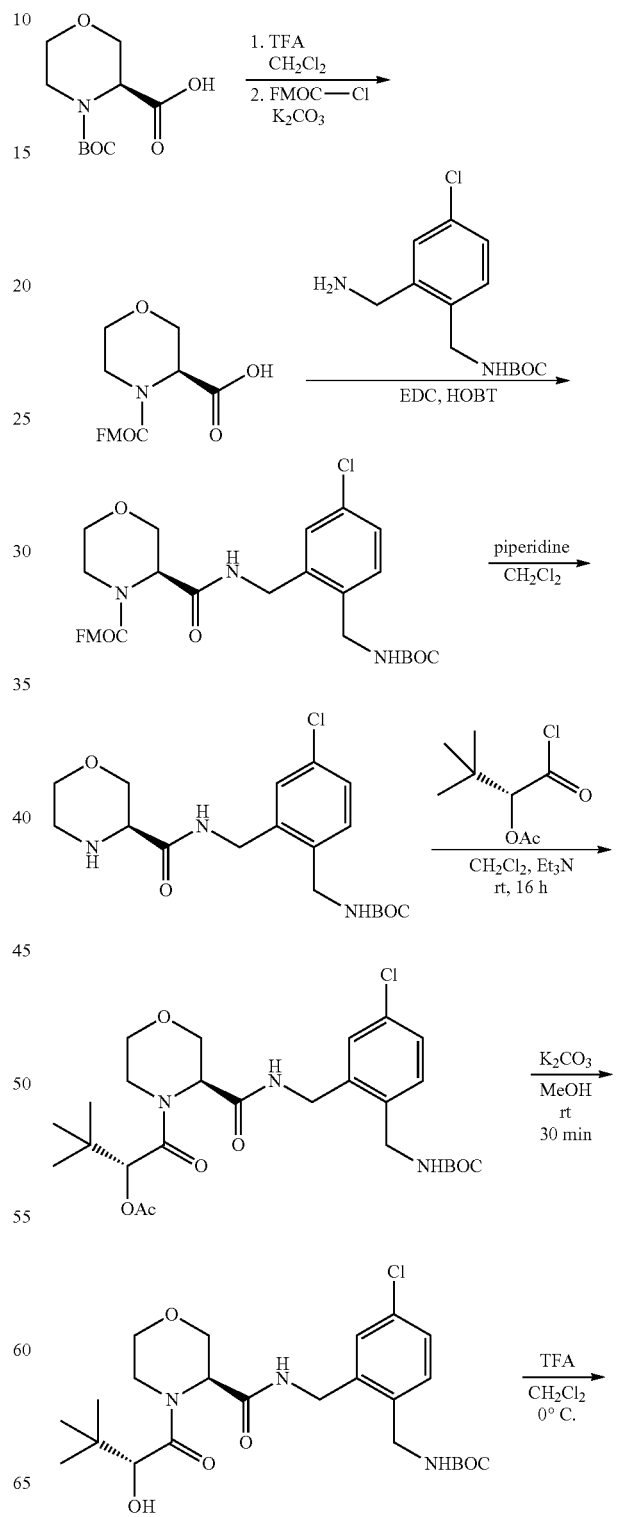

-continued

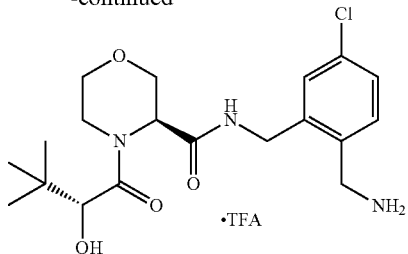

STEP 1: (S)-4-[{(9H-Fluoren-9-yl)methoxy}carbonyl]morpholine-3-carboxylic acid Trifluoroacetic acid (10 mL) was added to a solution of (S)-4-(tert-butoxycarbonyl) morpholine-3-carboxylic acid (5.00 g, 21.64 mmol) in $CH_2Cl_2$ (40 mL) dropwise at 0° C. and the reaction mixture was stirred at room temperature for 5 h. The reaction mixture was concentrated to dryness and the crude residue (2.80 g, 21.30 mmol) was dissolved in a mixture of dioxane (30 mL) and water (10 mL). The suspension was cooled to 0° C., FMOC-Cl (6.60 g, 25.60 mmol) and $K_2CO_3$ (11.60 g, 84.2 mmol) were added, and the mixture was stirred at room temperature for 3 h. The reaction mixture was concentrated, diluted with water (20 mL) and acidified with 1M aqueous HCl (30 mL) to pH 2-3. The resulting mixture was extracted with EtOAc (3×50 mL). The combined organic layers were washed with brine solution (50 mL), dried over anhydrous $Na_2SO_4$, filtered and concentrated under reduced pressure to afford the title compound (6.41 g) as colorless oil which was used in the next step without further purification.

STEP 2: (S)-(9H-Fluoren-9-yl)methyl-3-{(2-[{(tert-butoxycarbonyl)amino}methyl]-5-chlorobenzyl}carbamoyl]morpholine-4-carboxylate To a solution of (S)-4-[{(9H-Fluoren-9-yl)methoxy}carbonyl]morpholine-3-carboxylic acid (2.96 g, 8.39 mmol, 1.0 eq) in $CH_2Cl_2$ (10 mL), EDCI (3.20 g, 16.68 mmol, 2 eq.), HOBT (2.20 g, 16.28 mmol) and tert-butyl[2-(aminomethyl)-4-chlorobenzyl]carbamate (2.20 g, 8.39 mmol) were added at 0° C. The resulting mixture was stirred for 5 h at room temperature. The reaction mixture was diluted with $CH_2Cl_2$ (50 mL) and washed sequentially with saturated $NaHCO_3$ solution (20 mL) and 0.5 M aqueous HCl (20 mL). The organic layer was separated, washed with brine solution (20 mL), dried over anhydrous $Na_2SO_4$, filtered and concentrated under reduced pressure. The residue was purified by column chromatography (silica gel; eluent: 40% EtOAc/hexanes) to afford the title compound as pale yellow semi solid (4.10 g)

STEP 3: (S)-tert-Butyl-4-chloro-2-{(morpholine-3-carboxamido)methyl}benzylcarbamate Piperidine (4.5 mL, 45.2 mmol) was added to a solution of (S)-(9H-Fluoren-9-yl)methyl-3-{(2-[{(tert-butoxycarbonyl)amino}methyl]-5-chlorobenzyl}carbamoyl]morpholine-4-carboxylate (4.10 g, 67.6 mmol) in $CH_2Cl_2$ (20 mL) at 0° C. and the reaction mixture was stirred at room temperature for 1 h. The reaction mixture was concentrated to dryness and the residue was purified by reverse phase combiflash chromatography (C18; 10-100% acetonitrile/water) to afford the title compound as a white solid (1.61 g).

STEP 4: (R)-1-{(S)-3-[2-{(tert-Butoxycarbonylamino)methyl}-5-chlorobenzylcarbamoyl]morpholino}-3,3-dimethyl-1-oxobutan-2-yl acetate To a solution of (R)-2-acetoxy-3,3-dimethylbutanoic acid (0.14 g, 1.04 mmol) in $CH_2Cl_2$ (2 mL) was added oxalyl chloride (1.10 mL, 1.30 mmol) at 0° C. under nitrogen atmosphere and the resulting mixture was stirred at room temperature for 40 min. The reaction mixture was concentrated to dryness and the residue was dissolved in $CH_2Cl_2$ (4 mL). A solution of (S)-tert-Butyl-4-chloro-2-{(morpholine-3-carboxamido)methyl}benzylcarbamate (0.20 g, 0.52 mmol) and triethylamine (0.70 mL, 2.08 mmol) in $CH_2Cl_2$ (2 mL) was added dropwise at 0° C. and the reaction mixture was allowed to stir at room temperature for 16 h. The reaction mixture was diluted with $CH_2Cl_2$ (20 mL) and washed sequentially with saturated $NaHCO_3$ solution (10 mL) and 1M aqueous HCl (10 mL). The organic layer was washed with brine solution (10 mL), dried over anhydrous $Na_2SO_4$, filtered and concentrated under reduced pressure. The residue was purified by silica gel column chromatography (eluent: 50% EtOAc/hexanes) to afford the title compound as a pale yellow oil (0.2 g).

STEP 5: tert-Butyl 4-chloro-2-[{(S)-4-{(R)-2-hydroxy-3,3-dimethylbutanoyl}morpholine-3-carboxamido}methyl]benzylcarbamate $K_2CO_3$ (0.016 g, 0.11 mmol) was added to a solution of (R)-1-{(S)-3-[2-{(tert-Butoxycarbonylamino)methyl}-5-chlorobenzylcarbamoyl]morpholino}-3,3-dimethyl-1-oxobutan-2-yl acetate (0.28 g, 0.51 mmol) in MeOH (3 mL) and the reaction mixture was stirred at room temperature for 30 min. The reaction mixture was diluted with EtOAc (20 mL), acidified with 1N aqueous HCl (5 mL) and the extracted with EtOAc (2×20 mL). The combined organic layers were washed with brine solution (10 mL), dried over anhydrous $Na_2SO_4$, filtered and concentrated. The residue was purified by column chromatography (silica gel; eluent: 70% EtOAc/hexanes) to afford the title compound as a pale yellow oil (0.25 g).

STEP 6: (3S)—N-[2-(aminomethyl)-5-chlorobenzyl]-4-[(2R)-2-hydroxy-3,3-dimethylbutanoyl]morpholine-3-carboxamide trifluoroacetate salt Trifluoroacetic acid (50% solution in $CH_2Cl_2$, 3 mL) was added to a solution of tert-Butyl 4-chloro-2-[{(S)-4-{(R)-2-hydroxy-3,3-dimethylbutanoyl}morpholine-3-carboxamido}-methyl]-benzylcarbamate (0.25 g, 0.50 mmol) in $CH_2Cl_2$ (1 mL) and the reaction was stirred at 0° C. for 30 min. The reaction mixture was concentrated under reduced pressure and residue was triturated with diethyl ether to afford the title compound as a white hygroscopic solid. $^1$HNMR (400 MHz, $CD_3CN$): 8.37 (t, J=4.0 Hz, 1H), 8.05 (bs, 3H), 7.46-7.43 (m, 2H), 7.34 (dd, J=8.4 Hz, J=2.4 Hz, 1H), 4.78 (d, J=4.0 Hz, 1H), 4.46 (dd, J=15.2, 6.0 Hz, 1H), 4.39-4.43 (m, 3H), 4.22 (d, J=2.8 Hz, 2H), 3.91 (d, J=12.4 Hz, 2H), 3.86 (dd, J=11.6, 2.4 Hz, 1H), 3.58 (dd, J=8.4 Hz, J=4.0 Hz, 1H), 3.53-3.42 (m, 2H), 0.98 (s, 9H).

Ki (nM): 32

EXAMPLE 5

(3R)—N-[2-(aminomethyl)-5-chlorobenzyl]-4-[(2R)-2-hydroxy-3,3-dimethylbutanoyl]thiomorpholine-3-carboxamide trifluoroacetate salt

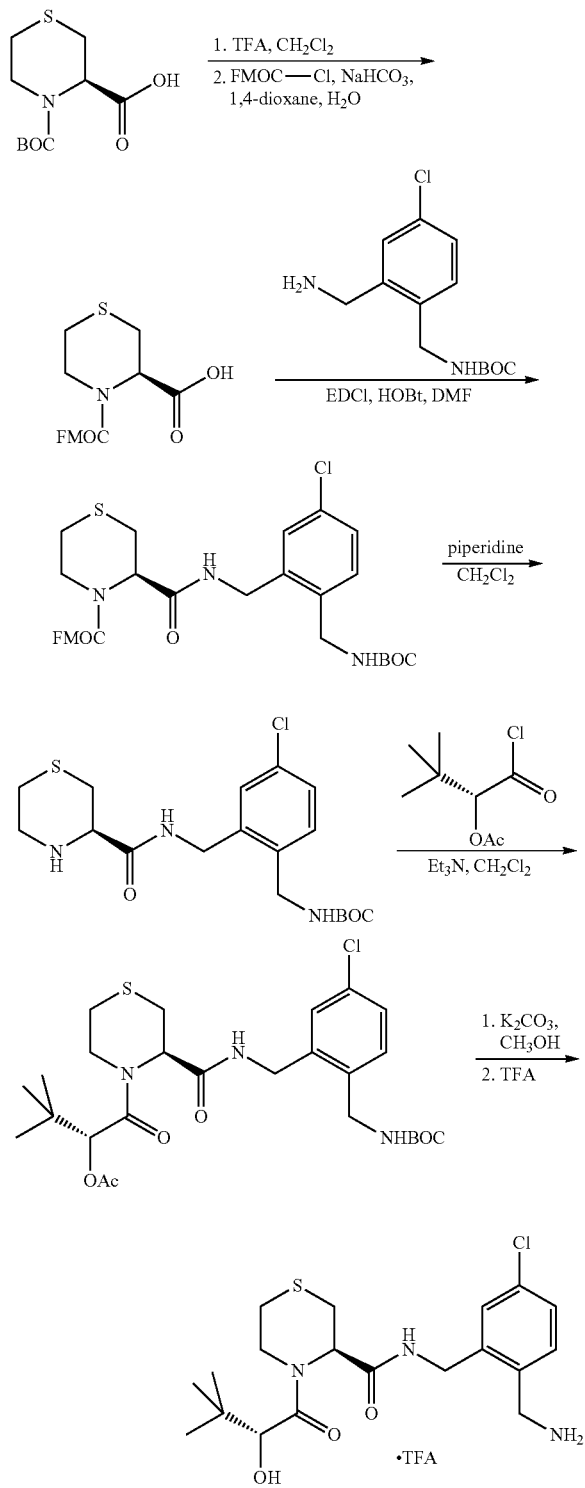

STEP 1: (R)-4-[{(9H-Fluoren-9-yl)methoxy}carbonyl]thiomorpholine-3-carboxylic acid Trifluoroacetic acid (4 mL, 23.5 mmol) was added to a stirred solution of (R)-4-(tert-butoxy carbonyl)thiomorpholine-3-carboxylic acid (1.0 g, 4.05 mmol) in $CH_2Cl_2$ (20 mL), and the reaction mixture was stirred at room temperature for 2 h. Volatile byproducts were removed at reduced pressure and the residue was concentrated from toluene (2×20 mL) and dried under high vacuum for 30 min. The crude residue was dissolved in 1,4-dioxane (10 mL) and water (10 mL) was added followed by $NaHCO_3$ (1.02 g, 12.15 mmol) and a solution of FMOC-Cl (1.04 g, 4.05 mmol) in 1,4-dioxane (10 mL). The reaction mixture was stirred at room temperature for 16 h. The mixture was concentrated under reduced pressure to remove volatile organic solvent and the residue was washed with MTBE (2×20 mL). The aqueous layer was acidified with 1N aqueous HCl to pH 2 and extracted with EtOAc (3×50 mL). The combined organic extracts were washed with brine solution (50 mL), dried over anhydrous $Na_2SO_4$, filtered and concentrated. The residue was purified by reverse phase column chromatography (C18; eluent: 10-100% acetonitrile/water) to afford the title compound (1.00 g) as a white semi-solid.

STEP 2: (R)-(9H-Fluoren-9-yl)methyl-3-[2-{(tert-butoxycarbonylamino)methyl}-5-chloro benzylcarbamoyl]thiomorpholine-4-carboxylate A mixture of (R)-4-[{(9H-Fluoren-9-yl)methoxy}carbonyl]thiomorpholine-3-carboxylic acid (1.0 g, 2.71 mmol), amine (0.73 g, 2.71 mmol), HOBT (0.44 g, 3.25 mmol), EDC.HCl (0.62 g, 3.25 mmol), and DIPEA (1.42 mL, 8.13 mmol) in DMF (20 mL) was stirred at room temperature for 16 h. The reaction mixture was diluted with EtOAc (50 mL) and washed sequentially with saturated aqueous $NaHCO_3$ solution (20 mL) and brine solution (2×20 mL). The organic layer was separated, dried over anhydrous $Na_2SO_4$, filtered and concentrated under reduced pressure. The residue was purified by combiflash column chromatography (silica gel; eluent: 30% EtOAc/hexanes) to afford the title compound (1.20 g) as white solid.

STEP 3: (R)-tert-Butyl-4-chloro-2-{(thiomorpholine-3-carboxamido)-methyl}-benzyl-carbamate Piperidine (0.95 mL, 9.65 mmol) was added dropwise to a stirred solution of (R)-(9H-Fluoren-9-yl)methyl-3-[2-{(tert-butoxycarbonylamino)methyl}-5-chloro benzylcarbamoyl]thiomorpholine-4-carboxylate (1.20 g, 1.93 mmol) in $CH_2Cl_2$ (50 mL) and the resulting mixture was stirred at room temperature for 2 h. Volatile solvent was removed under reduced pressure and the residue was purified by reverse phase combiflash column chromatography (C18; eluent: 10-100% acetonitrile:water) to afford the title compound (0.64 g) as a white solid.

STEP 4: (R)-1-{(R)-3-[2-{(tert-Butoxycarbonylamino)methyl}-5-chlorobenzylcarbamoyl]thiomorpholino)-3,3-dimethyl-1-oxobutan-2-yl acetate To a solution of (R)-tert-Butyl-4-chloro-2-{(thiomorpholine-3-carboxamido)-methyl}-benzyl-carbamate (0.56 g, 1.40 mmol) in $CH_2Cl_2$ (25 mL) was added triethyl amine (0.59 mL, 4.2 mmol) and solution of (2R)-1-chloro-3,3-dimethyl-1-oxobutan-2-yl acetate (0.496 g, 2.8 mmol) in $CH_2Cl_2$ (5 mL) dropwise at −10° C. and the resulting mixture was allowed to warm up to room temperature over 1 h. The reaction mixture was quenched with water (50 mL) and extracted with EtOAc (3×25 mL). The combined organic layers were washed with brine solution, dried over anhydrous $Na_2SO_4$, filtered and concentrated under reduced pressure. The residue was purified by reverse phase combiflash column chromatography (C18; eluent: 10-100% acetonitrile/water) to obtain the title compound (0.42 g) as a white solid.

STEP 5: (3R)—N-[2-(aminomethyl)-5-chlorobenzyl]-4-[(2R)-2-hydroxy-3,3-dimethylbutanoyl]thiomorpholine-3-carboxamide trifluoroacetate (salt)

Solid $K_2CO_3$ (5.8 mg, 0.042 mmol) was added to the solution of (R)-1-{(R)-3-[2-{(tert-Butoxycarbonylamino)methyl}-5-chlorobenzylcarbamoyl]thiomorpholino)-3,3-dimethyl-1-oxo-butan-2-yl acetate (0.12 g, 0.21 mmol) in MeOH (5 mL) and the reaction mixture was stirred at room temperature for 30 min. The reaction mixture was diluted with EtOAc (50 mL) and washed with 0.1M aqueous HCl (20 mL), water (2×20 mL), and brine solution (20 mL). The organic layer was dried over anhydrous $Na_2SO_4$, filtered and concentrated under reduced pressure. The residue was purified by reverse phase combiflash column chromatography (C18; eluent: 10-100% acetonitrile/water) to afford the intermediate BOC-protected alcohol as an off-white solid (0.092 g, crude). The crude intermediate was dissolved in $CH_2Cl_2$ (3 mL) then trifluoroacetic acid (1.0 mL, 13.42 mmol) was added and the resulting mixture was stirred at room temperature for 2 h. Volatile byproducts were removed under vacuum and the residue was purified by reverse phase combiflash column chromatography (C18; eluent: 10-100% acetonitrile:water) to afford the title compound as a white solid. $^1H$ NMR (MeOD 400 MHz) (δ) ppm: 7.41 (s, 1H); 7.39-7.35 (m, 2H); 5.28 (t, J=4.4 Hz, 1H); 4.54-4.38 (m, 3H); 4.28-4.21 (m, 3H); 3.61-3.54 (m, 1H); 3.18-3.12 (m, 1H); 2.93-2.88 (m, 1H); 2.82-2.75 (m, 1H); 2.62-2.59 (m, 1H), 0.98 (m, 9H).

Ki (nM): 1.1

EXAMPLE 6

3R)—N-[2-(aminomethyl)-5-chlorobenzyl]-4-[(2R)-2-hydroxy-3,3-dimethylbutanoyl]thiomorpholine-3-carboxamide 1-oxide trifluoroacetate (salt

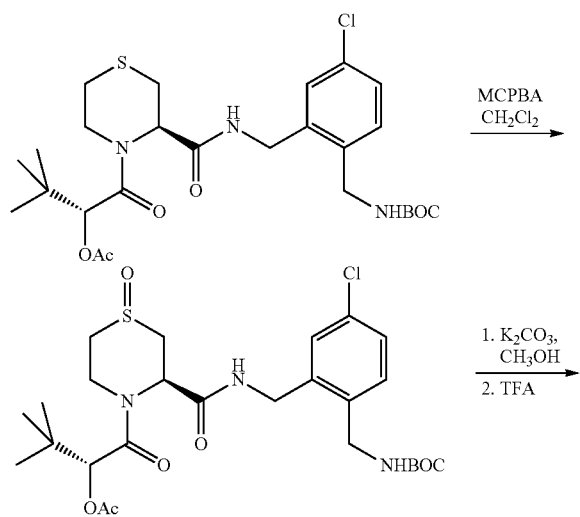

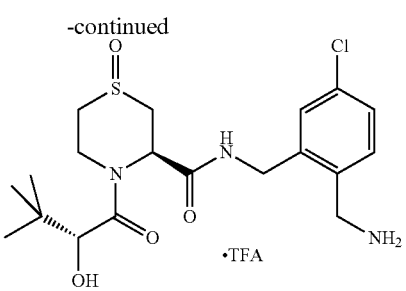

STEP 1: (R)-1-{(R)-3-[2-{(tert-Butoxycarbonylamino)methyl}-5-chlorobenzylcarbamoyl]-S-4-oxo-thiomorpholino}-3,3-dimethyl-1-oxobutan-2-yl acetate m-Chloroperbenzoic acid (0.039 g, 0.22 mmol) was added to the solution of (R)-1-{(R)-3-[2-{(tert-Butoxycarbonylamino)methyl}-5-chlorobenzylcarbamoyl]thiomorpholino}-3,3-dimethyl-1-oxobutan-2-yl acetate (0.10 g, 0.25 mmol) in $CH_2Cl_2$ (5 mL) and the reaction mixture was stirred at room temperature for 30 min. The reaction was quenched by addition of saturated aqueous $Na_2S_2O_5$ solution (20 mL) and 10% aqueous $NaHCO_3$ (20 mL). The organic layer was separated and the aqueous layer was extracted with $CH_2Cl_2$ (2×20 mL). The combined organic layers were washed with brine solution (50 mL), dried over anhydrous $Na_2SO_4$, and concentrated under reduced pressure. The residue was purified by reverse phase combiflash column chromatography (C18; eluent: 10-100% acetonitrile/water) to the title compound (0.10 g) as a white solid.

STEP 2: (3R)—N-[2-(aminomethyl)-5-chlorobenzyl]-4-[(2R)-2-hydroxy-3,3-dimethylbutanoyl]thiomorpholine-3-carboxamide 1-oxide trifluoroacetate (salt)

Solid $K_2CO_3$ (4.7 mg, 0.034 mmol) was added to the solution of (R)-1-{(R)-3-[2-{(tert-Butoxycarbonylamino)methyl}-5-chlorobenzylcarbamoyl]-S-4-oxo-thiomorpholino}-3,3-dimethyl-1-oxobutan-2-yl acetate (0.10 g, 0.17 mmol) in MeOH (5 mL) and the resulting mixture was stirred at room temperature for stirred for 30 min. The reaction mixture was diluted with EtOAc (50 mL) and washed with 0.1M aqueous HCl (20 mL), water (2×20 mL), and brine solution (20 mL). The organic layer was dried over anhydrous $Na_2SO_4$, filtered and concentrated under reduced pressure. The residue was purified by reverse phase combiflash column chromatography (C18; eluent: 10-100% acetonitrile/water) to afford the intermediate BOC-protected alcohol as an off-white solid (0.06 g, crude). The crude intermediate was dissolved in in $CH_2Cl_2$ (2 mL) then trifluoroacetic acid (1.0 mL, 13.42 mmol) was added. The reaction mixture was stirred at room temperature for 2 h then volatile byproducts were removed under reduced pressure residue. The residue was purified by reverse phase combiflash column chromatography (C18; eluent: 10-100% acetonitrile/water) to afford the title compound as a white solid. $^1H$ NMR (MeOD-$d_4$, 400 MHz, mixture of rotamers), (δ) ppm: 7.41 (s, 1H), 7.39-7.35 (m, 2H), 5.28 (t, J=4.4 Hz, 1H), 4.54-4.38 (m, 3H), 4.28-4.21 (m, 3H), 3.61-3.54 (m, 1H), 3.18-3.12 (m, 1H), 2.93-2.88 (m, 1H), 2.82-2.75 (m, 1H), 2.62-2.59 (m, 1H), 0.98 (s, 9H).

Ki (nM): 78

EXAMPLE 7

(3R)—N-[2-(aminomethyl)-5-chlorobenzyl]-4-[(2R)-2-hydroxy-3,3-dimethylbutanoyl]thiomorpholine-3-carboxamide 1,1-dioxide trifluoroacetate salt

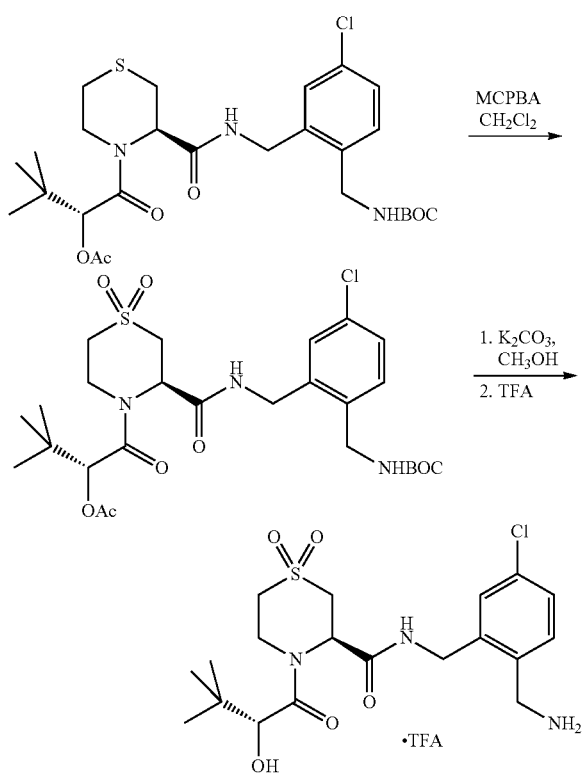

STEP 1: (R)-[{(9H-Fluoren-9-yl)methoxy}carbonyl]-S-4,4-dioxide-thiomorpholine-3-carboxylic acid m-Chloroperbenzoic acid (0.155 g, 0.9 mmol) was added to the solution of (R)-1-{(R)-3-[2-{(tert-Butoxycarbonylamino)methyl}-5-chlorobenzylcarbamoyl]thiomorpholino}-3,3-dimethyl-1-oxobutan-2-yl acetate (0.2 g, 0.36 mmol) in $CH_2Cl_2$ (5 mL), and the reaction mixture was stirred at room temperature for 4 h. The reaction was quenched by addition of saturated aqueous $Na_2S_2O_5$ solution (20 mL) and 10% aqueous $NaHCO_3$ (20 mL). The organic layer was separated and the aqueous layer was extracted with $CH_2Cl_2$ (2×20 mL). The combined organic extract was washed with brine solution (50 mL), dried over anhydrous $Na_2SO_4$ and concentrated under reduced pressure. The residue was purified by reverse phase combiflash column chromatography (C18; eluent: 10-100% acetonitrile/water) to provide afford the title compound (0.14 g) as a white solid.

STEP 2: (3R)—N-[2-(aminomethyl)-5-chlorobenzyl]-4-[(2R)-2-hydroxy-3,3-dimethylbutanoyl]thiomorpholine-3-carboxamide 1,1-dioxide trifluoroacetate salt Solid $K_2CO_3$ (6.62 mg, 0.048 mmol) was added to the solution of (R)-4-[{(9H-Fluoren-9-yl)methoxy}carbonyl]-S-4,4-dioxide-thiomorpholine-3-carboxylic acid (0.14 g, 0.24 mmol) in MeOH (5 mL) and the reaction mixture was stirred at room temperature for stirred for 30 min. The reaction mixture was diluted with ethyl acetate (50 mL) and washed sequentially with 0.1M aqueous HCl (20 mL), water (2×20 mL), and brine solution (20 mL). The organic layer was dried over anhydrous $Na_2SO_4$, filtered and concentrated under reduced pressure. The residue was purified by reverse phase combiflash column chromatography (C18; eluent: 10-100% acetonitrile:water) to afford the intermediate BOC-protected alcohol as an off-white solid (0.065 g, crude). The crude intermediate was dissolved in $CH_2Cl_2$ (2 mL) and trifluoro acetic acid (0.5 mL, 6.71 mmol) was added. The reaction mixture was stirred at room temperature for 2 hours then volatile byproducts were removed under reduced pressure residue. The residue was purified by reverse phase combiflash column chromatography (C18; eluent: 10-100% acetonitrile/water) to afford the title compound as a white solid. $^1$H NMR (MeOD-$d_4$, 400 MHz, mixture of rotamers), (δ) ppm: 7.49-7.38 (m, 3H), 5.88-5.47 (m, 1H), 4.58-4.22 (m, 5H), 4.15-3.71 (m, 2H), 3.52-3.35 (m, 2H), 3.16-3.01 (m, 2H), 0.98 (br s, 9H).

Ki (nM): 52

In Vitro Assay for Determining Proteinase Inhibition

Relevant in vitro assays are referenced in Morrissette, et al., Bioorg. Med. Chem. Lett. 2004, 14, 4161-4164 and described in Lewis, et al. Thromb. Res. 1993, 70, 173 (assays of human α-thrombin and human trypsin), and Lewis, et al. Thromb. Haemostasis 1995, 74, 1107-1112. The assays were carried out at 25° C. in 0.05 M TRIS buffer pH 7.4, 0.15 M NaCl, 0.1% PEG. Trypsin assays also contained 1 mM $CaCl_2$. In assays wherein rates of hydrolysis of a p-nitroanilide (pna) substrate were determined, a Thermomax 96-well plate reader was used was used to measure (at 405 nm) the time dependent appearance of p-nitroaniline. sar-PR-pna was used to assay human α-thrombin ($K_m$=125 μM) and bovine trypsin ($K_m$=125 μM). p-Nitroanilide substrate concentration was determined from measurements of absorbance at 342 nm using an extinction coefficient of 8270 $cm^{-1}M^{-1}$.

In certain studies with potent inhibitors ($K_i$<10 nM) where the degree of inhibition of thrombin was high, a more sensitive activity assay was employed. In this assay the rate of thrombin catalyzed hydrolysis of the fluorogenic substrate benzyloxycarbonyl-Gly-Pro-Arg-7-amino-4-trifluoromethylcoumarin (Z-GPR-afc, Lewis S. D. et al. (1998) J. Biol. Chem. 273, pp. 4843-4854) ($K_m$=27 μM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration ≤0.1 $K_m$ into a solution containing enzyme or enzyme equilibrated with inhibitor. Times required to achieve equilibration between enzyme and inhibitor were determined in control experiments. Initial velocities of product formation in the absence ($V_O$) or presence of inhibitor ($V_i$) were measured. Assuming competitive inhibition, and that unity is negligible compared $K_m$/[S], [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_O/V_i$ on [I] shown in the following equation.

$$V_O/V_i = 1 + [I]/K_i$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels.

EXAMPLE 8

Tablets containing 25.0, 50.0, and 100.0 mg., respectively, of the following active compounds are prepared as illustrated below (compositions A-C). Active I is (2S)—N-[2-(aminomethyl)-5-chlorobenzyl]-1-[(2R)-2-hydroxy-3,3-dimethylbutanoyl]-piperidine-2-carboxamide trifluoroacetate salt.

|  | Amount-(mg) | | |
| --- | --- | --- | --- |
| Component | A | B | C |
| Active I | 25 | 50 | 100 |
| Microcrystalline cellulose | 37.25 | 100 | 200 |
| Modified food corn starch | 37.25 | 4.25 | 8.5 |
| Magnesium stearate | 0.5 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 9

Tablet Preparation

Exemplary compositions of (2S)—N-[2-(aminomethyl)-5-chlorobenzyl]-1-[(2R)-2-hydroxy-3,3-dimethylbutanoyl]-piperidine-2-carboxamide trifluoroacetate salt (Active I) tablets are shown below:

| Component | 0.25 mg | 2 mg | 10 mg | 50 mg |
| --- | --- | --- | --- | --- |
| Active I | 0.500% | 1.000% | 5.000% | 14.29% |
| mannitol | 49.50% | 49.25% | 47.25% | 42.61% |
| microcrystalline cellulose | 49.50% | 49.25% | 47.25% | 42.61% |
| magnesium stearate | 0.500% | 0.500% | 0.500% | 0.500% |

2, 10 and 50 mg tablets were film-coated with an aqueous dispersion of hydroxypropyl cellulose, hydroxypropyl methylcellulose and titanium dioxide, providing a nominal weight gain of 2.4%.

Active I, mannitol and microcrystalline cellulose were sieved through mesh screens of specified size (generally 250 to drug was uniformly distributed in the resulting dry powder blend. Magnesium stearate was screened and added to the blender, after which a precompression tablet blend was achieved upon additional mixing (typically 2 to 10 min) The precompression tablet blend was then compacted under an applied force, typically ranging from 0.5 to 2.5 metric tons, sufficient to yield tablets of suitable physical strength with acceptable disintegration times (specifications will vary with the size and potency of the compressed tablet). In the case of the 2, 10 and 50 mg potencies, the tablets were dedusted and film-coated with an aqueous dispersion of water-soluble polymers and pigment.

Alternatively, a dry powder blend is compacted under modest forces and remilled to afford granules of specified particle size. The granules are then mixed with magnesium stearate and tableted as stated above.

EXAMPLE 10

Intravenous formulations of (2S)—N-[2-(aminomethyl)-5-chlorobenzyl]-1-[(2R)-2-hydroxy-3,3-dimethylbutanoyl]-piperidine-2-carboxamide trifluoroacetate salt (Active I) were prepared according to general intravenous formulation procedures.

750 μm) and combined in a suitable blender. The mixture was subsequently blended (typically 15 to 30 min) until the

| Component | Estimated range |
| --- | --- |
| Active I | 0.12-0.50 mg |
| D-glucuronic acid | 0.5-5 mg |
| Mannitol NF | 50-53 mg |
| 1N Sodium Hydroxide | q.s. pH 3.9-4.1 |
| Water for injection | q.s. 1.0 mL |

Various other buffer acids, such as L-lactic acid, acetic acid, citric acid or any pharmaceutically acceptable acid/conjugate base with reasonable buffering capacity in the pH range acceptable for intravenous administration may be substituted for glucuronic acid.

What is claimed is:

1. A compound of the formula I

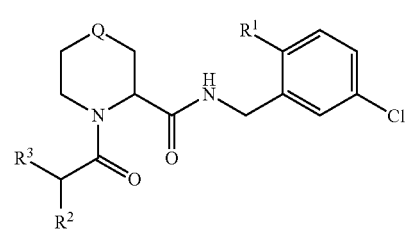

(I)

or a pharmaceutically acceptable salt thereof, wherein

Q is S, S(O) or S(O$_2$);

R$^1$ is a heterocycle or —(CR$^5$R$^6$)$_{1\text{-}2}$NH$_2$, wherein R$^5$ and R$^6$, each time in which they occur, are independently H, C$_{1\text{-}6}$ alkyl, —CH$_2$F, —CHF$_2$, CF$_3$ or —CH$_2$OH;

R$^2$ is OH, NH$_2$ or NHSO$_2$CH$_3$; and

R$^3$ is C$_{1\text{-}6}$ alkyl.

2. A compound of claim 1, or a pharmaceutically acceptable salt thereof, having the formula Ia

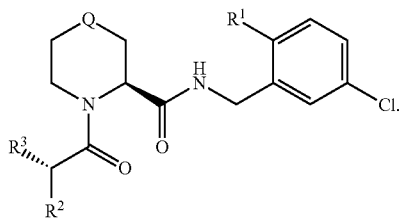

(Ia)

3. A compound of claim 1, or a pharmaceutically acceptable salt thereof, wherein $R^1$ is tetrazole or —$CH_2NH_2$.
4. A compound of claim 3, or a pharmaceutically acceptable salt thereof, wherein $R^1$ is —$CH_2NH_2$.
5. A compound of claim 1, or a pharmaceutically acceptable salt thereof, wherein $R^2$ is OH.
6. A compound of claim 1, or a pharmaceutically acceptable salt thereof, wherein $R^3$ is —$C(CH_3)_3$.
7. A compound of claim 1, or a pharmaceutically acceptable salt thereof, wherein $R^5$ is H.
8. A compound of claim 1, or a pharmaceutically acceptable salt thereof, wherein $R^6$ is H.
9. A compound of claim 2, or a pharmaceutically acceptable salt thereof, having the formula Ib

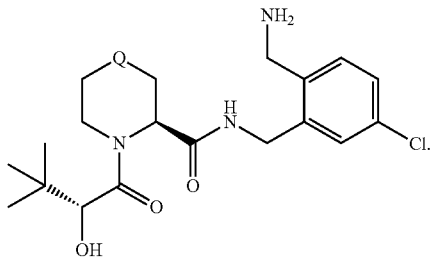

(Ib)

10. A compound of claim 1, or pharmaceutically acceptable salt thereof, which is
    - (3R)—N-[2-(aminomethyl)-5-chlorobenzyl]-4-[(2R)-2-hydroxy-3,3-dimethylbutanoyl]thiomorpholine-3-carboxamide,
    - (3R)—N-[2-(aminomethyl)-5-chlorobenzyl]-4-[(2R)-2-hydroxy-3,3-dimethylbutanoyl]thiomorpholine-3-carboxamide 1-oxide, or
    - (3R)—N-[2-(aminomethyl)-5-chlorobenzyl]-4-[(2R)-2-hydroxy-3,3-dimethylbutanoyl]thiomorpholine-3-carboxamide 1,1-dioxide.

11. A salt of claim 10 which is
    - (3R)—N-[2-(aminomethyl)-5-chlorobenzyl]-4-[(2R)-2-hydroxy-3,3-dimethylbutanoyl]thiomorpholine-3-carboxamide trifluoroacetate,
    - (3R)—N-[2-(aminomethyl)-5-chlorobenzyl]-4-[(2R)-2-hydroxy-3,3-dimethylbutanoyl]thiomorpholine-3-carboxamide 1-oxide trifluoroacetate, or
    - (3R)—N-[2-(aminomethyl)-5-chlorobenzyl]-4-[(2R)-2-hydroxy-3,3-dimethylbutanoyl]thiomorpholine-3-carboxamide 1,1-dioxide trifluoroacetate.

12. A pharmaceutical composition comprising a compound of claim 1 or a pharmaceutically acceptable salt thereof and a pharmaceutically acceptable carrier.
13. A method for inhibiting thrombin in blood comprising adding to the blood a composition of claim 12.
14. A method for inhibiting formation of blood platelet aggregates in blood comprising adding to the blood a composition of claim 12.
15. A method for inhibiting thrombus formation in blood comprising adding to the blood a composition of claim 12.
16. A method for treating venous thromboembolism and pulmonary embolism in a mammal comprising administering to the mammal a composition of claim 12.
17. A method for treating deep vein thrombosis in a mammal comprising administering to the mammal a composition of claim 12.
18. A method for treating thromboembolic stroke in humans and other mammals comprising administering to the mammal a composition of claim 12.

\* \* \* \* \*